(12) United States Patent
Sohrab

(10) Patent No.: US 6,549,796 B2
(45) Date of Patent: Apr. 15, 2003

(54) MONITORING ANALYTE CONCENTRATION USING MINIMALLY INVASIVE DEVICES

(75) Inventor: Borzu Sohrab, Los Altos, CA (US)

(73) Assignee: LifeScan, Inc., Milpitas, CA (US)

( * ) Notice: Subject to any disclaimer, the term of this patent is extended or adjusted under 35 U.S.C. 154(b) by 0 days.

(21) Appl. No.: 09/865,826

(22) Filed: May 25, 2001

(65) Prior Publication Data

US 2002/0177764 A1 Nov. 28, 2002

(51) Int. Cl.⁷ .............................................. A61B 05/05
(52) U.S. Cl. ........................................ 600/345; 600/575
(58) Field of Search ................................. 600/345, 347, 600/575, 583, 584; 606/181

(56) References Cited

U.S. PATENT DOCUMENTS

| | | | |
|---|---|---|---|
| 4,627,445 A | * 12/1986 | Garcia et al. | 600/583 |
| 4,637,403 A | * 1/1987 | Garcia et al. | 600/368 |
| 4,680,628 A | 7/1987 | Wojcik et al. | |
| 4,721,677 A | 1/1988 | Clark, Jr. | |
| 4,787,398 A | * 11/1988 | Garcia et al. | 600/583 |
| 4,995,402 A | * 2/1991 | Smith et al. | 206/569 |
| 5,002,054 A | 3/1991 | Ash et al. | |
| 5,108,819 A | 4/1992 | Heller et al. | |
| 5,161,532 A | 11/1992 | Joseph | |
| 5,390,671 A | 2/1995 | Lord et al. | |
| 5,582,184 A | 12/1996 | Erickson et al. | |
| 5,682,233 A | 10/1997 | Brinda | |
| 5,746,217 A | 5/1998 | Erickson et al. | |
| 5,820,570 A | 10/1998 | Erickson et al. | |
| 5,879,310 A | 3/1999 | Sopp et al. | |
| 5,971,941 A | * 10/1999 | Simons et al. | 600/573 |
| 6,056,701 A | * 5/2000 | Duchon et al. | 600/573 |
| 6,056,738 A | * 5/2000 | Marchitto et al. | 600/573 |
| 6,086,545 A | 7/2000 | Roe et al. | 600/573 |
| 6,091,975 A | 7/2000 | Daddona et al. | |
| 6,099,484 A | * 8/2000 | Douglas et al. | 600/583 |
| 6,155,992 A | 12/2000 | Henning et al. | |
| 6,183,489 B1 | * 2/2001 | Douglas et al. | 600/583 |
| 6,302,855 B1 | * 10/2001 | Lav et al. | 600/584 |
| 6,375,626 B1 | * 4/2002 | Allen et al. | 600/573 |

FOREIGN PATENT DOCUMENTS

| | | |
|---|---|---|
| DE | 4234553 A1 | * 10/1992 |
| WO | WO 93/22453 | 11/1993 |
| WO | WO 01/64105 A1 | 3/2001 |

* cited by examiner

*Primary Examiner*—Lisa A. Douglas
(74) *Attorney, Agent, or Firm*—Carol M. LaSalle; Bozicevic, Field & Francis, LLP

(57) ABSTRACT

A method of monitoring the concentration of an analyte in a host or portion thereof over a given period of time. The method includes the steps of: (a) making a first analyte concentration measurement at a first point of time using a single use analyte concentration measuring device; (b) making a second analyte concentration measurement at a second point in time using a single use analyte concentration measuring device; and (c) making one or more additional analyte concentration measurements using another single use measuring device, wherein the analyte concentration measurements are made according to a selected schedule to monitor the concentration of analyte in a host over a given portion of time.

19 Claims, No Drawings

MONITORING ANALYTE CONCENTRATION USING MINIMALLY INVASIVE DEVICES

INTRODUCTION

1. Field of the Invention

The field of this invention is analyte determination.

2. Background

Analyte detection in physiological fluids, e.g., blood or blood derived products, interstitial fluid, etc., is of ever increasing importance to today's society. Analyte detection assays find use in a variety of applications, including clinical laboratory testing, home testing, etc., where the results of such testing play a prominent role in diagnosis and management in a variety of disease conditions. Analytes of interest include glucose for diabetes management, cholesterol, and the like. In response to this growing importance of analyte detection, a variety of analyte detection protocols and devices for both clinical and home use have been developed.

Historically, blood glucose and other bodily analyte measurements were invasive. Such measurements were generally made by withdrawing a blood sample and measuring the desired analyte within the blood or plasma. Blood samples were typically withdrawn by inserting a needle into a major artery or, more commonly, a vein. Such direct vascular blood sampling employed by these early methods had several limitations, including pain, hematoma and other bleeding complications, and infection. In addition, due to the vascular damage resulting from the needle puncture, sampling could not be repeated on a routine basis. Finally, it was extremely difficult for patients to perform a direct vascular puncture on themselves.

A more recent technique that has been developed to overcome some of the disadvantages associated with the above protocols is to collect a blood sample by cutting or lancing the skin and the subcutaneous tissue, including the small, underlying blood vessels, to produce a localized bleeding on the body surface. A lancet, knife, or other cutting device is required. The blood on the body surface is then collected into a small tube or other container. The fingertip is the most frequently used site to collect blood in this method due to the large number of small blood vessels located in the region. One method is shown in U.S. Pat. No. 4,637,403. This sampling method also suffers from several major disadvantages, including pain and the potential for infection and other problems associated with repeated sampling for a confined area. Pain is a major disadvantage since the fingertip has a large concentration of nerve endings. Also, there is a limited body surface area from which to take these samples and measurement on a high frequency basis.

Because the above described prior art invasive techniques are painful, patients frequently avoid having blood glucose measured. For diabetics, the failure to measure blood glucose on a prescribed basis can be very dangerous. Also, the invasive techniques, which result in lancing blood vessels, create an enhanced risk for disease transmission.

Attempts have been made to develop glucose and other analyte sensors for implantation in the human body. Advantages of such implanted sensors include the ability to provide "continuous," chronic monitoring without having to consciously sample blood at each measuring event. Despite the many potential advantages provided by implanted sensors, development of a permanently implanted or long-term, chronic implanted sensor has been unsuccessful. Attempts to develop short-term implantable sensors (up to 2–3 days) have also met with very limited success. Most implantable sensors are based on measuring various products from chemical reactions between agent(s) located on or within the sensor and the desired analyte. Implanted glucose sensors have typically used the glucose oxidase reaction to measure the amount of glucose, as described in U.S. Pat. No. 5,108,819. Such implanted glucose sensors have been intended for insertion through the epidermis and dermis to the subcutaneous tissue. An alternative location previously described for chronic sensor implant is the peritoneal cavity. Implanted sensors typically require direct or telemetered connection to a measurement instrument, usually located external the body.

All implanted sensors are faced with several major problems. First, all foreign materials, including materials incorporated into a glucose sensor, produce unwanted body reactions. Such reactions include the formation of fibrotic tissue around the sensor which alters the sensor's contact with normal body fluids and analytes, such as glucose. The body's natural defense mechanism may also have a direct "poisoning" effect upon the sensor's operation by interfering with the chemical reactions required by chemical-based sensors. As with any implanted object, implanted sensors may also initiate other bodily reactions including inflammation, pain, tissue necrosis, infection, and other unwanted reactions.

Implanted sensors require certain chemicals and chemical reactions to determine the level of analyte in the surrounding medium. These chemical reactions are the source of the other major problem facing any implantable sensor. Chemically-based sensors require products to be consumed and other products to be produced as part of the sensor's normal operations. Therefore, the sensors can quickly be depleted of the chemical agents required to sustain the desired chemical reactions. Secondly, by-products are given off as a result of the basic chemical reaction. These by-products often "poison" the sensor or cause other unwanted tissue reactivity. Because of these severe limitations, implanted sensors are not practical. Finally, such implanted sensors are painful to implant and are a source of infection.

As such, while offering benefits over traditional analyte measurement devices and protocols, such as continual, automated monitoring of the analyte of interest, implantable analyte concentration measurement devices currently available are unsatisfactory for a number of reasons.

Accordingly, there is a continued interest in the development of new analyte concentration measurement protocols and devices. Of particular interest would be the development of a continuous analyte concentration measurement system that does not suffer from disadvantages experienced with implantable sensors, as reviewed above.

3. Relevant Literature

U.S. Patents of interest include: U.S. Pat. Nos. 4,680,628; 4,721,677; 5,002,054; 5,108,819; 5,161,532; 5,390,671, 5,582,184; 5,682,233; 5,746,217; 5,820,520; 5,879,310; 6,056,738; 6,086,545; 6,091,975; and 6,155,992.

SUMMARY OF THE INVENTION

In accordance with the present invention there is provided a method for determining the analyte concentration in a host over a period of time. The method comprising the steps of: (a) making a first analyte concentration measurement at a first point of time using a single use analyte concentration measuring device; (b) making a second analyte concentration measurement at a second point in time using a single use analyte concentration measuring device; and (c) making one or more additional analyte concentration measurements using another single use measuring device, wherein the analyte concentration measurements are made according to a selected schedule to monitor the concentration of analyte in a host over a given portion of time.

In accordance with the present invention there is provided a method of monitoring the concentration of glucose in interstitial fluid of a host over a given period of time. The method comprising the steps of: (a) making a first interstitial fluid glucose concentration measurement at a first point in a time period using a single use interstitial fluid glucose concentration measurement device; (b) making a second interstitial fluid glucose concentration measurement at a second point in the time period using a single use interstitial fluid glucose concentration measurement device; and (c) making one or more additional interstitial fluid glucose concentration measurements according to a predetermined schedule to monitor the concentration of glucose over a period of time.

In accordance with the present invention there is provided a system for use in monitoring the concentration of analyte in a host over a portion of time, the system comprising a removable cartridge, the cartridge includes at lease a first and second single use analyte concentration measuring devices. The system further includes a device into which the cartridge may be inserted, wherein the device includes an activation means for selectively activating the first and second measurement devices of the cartridge according to a predetermined schedule.

In accordance with the present invention there is provided a kit for use in monitoring the concentration of an analyte in a host over a given period of time. The kit includes a removable cartridge; the cartridge includes at lease a first and second single use analyte concentration measuring devices. The system further includes a device into which the cartridge may be inserted, wherein the device includes an activation means for selectively activating the first and second measurement devices of the cartridge according to a predetermined schedule.

DESCRIPTION OF THE SPECIFIC EMBODIMENTS

Methods and devices are provided for automatically monitoring the concentration of an analyte in a host or portion thereof, i.e., for automatically measuring the concentration of an analyte at two or more points over a given time period. In the subject methods, substantially painless single use analyte concentration detection devices are employed to measure the concentration of the analyte of interest in the host, or portion thereof, e.g., interstitial fluid, where the measurements take place automatically according to a predetermined schedule. Devices provided by the subject invention have at least two different substantially painless single use analyte concentration measurement components that are under the control of an activation means that activates the measurement components according to a schedule. Various types of measurement scheduling modes are employable with the present invention. For example, the schedule may be predetermined according to either fixed times of day or fixed intervals of time. The schedule may otherwise be "adaptive" in response to immediate or short-term (i.e., within hours) preceding data. Another type of scheduling is one that is "predictive" in response to previous data collected over a longer period (i.e., over one or more days). The present invention may also provide an "on-demand" mode where the physician or patient may override the programmed measurement schedule and activate measurement of the target analyte.

Also provided are systems and kits for use in practicing the subject methods. The subject methods find use in monitoring the concentration of a variety of different analytes of interest, and are particularly suited for use in monitoring the concentration of glucose in interstitial fluid.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, singular references include the plural, unless the context clearly dictates otherwise. Unless defined otherwise, all technical and scientific terms used herein have the same meaning as commonly understood to one of ordinary skill in the art to which this invention belongs.

Methods

As summarized above, the subject invention is directed to methods and devices for monitoring the concentration of an analyte of interest in a host or portion thereof. By monitoring is meant that the concentration of the analyte of interest is measured two or more times over a given time period, such that two or more measurements of the analyte concentration are obtained for a given time period. The given period of time may vary from 1 hour to several hours, to days. However, the given period of time typically ranges from about 1 hour to 2 days, and is often 2 to 8 hours. Measuring the analyte concentration at least twice during the given time period provides for the monitoring of the analyte concentration during the time period.

A feature of the subject methods is that the monitoring is automatic. In characterizing the monitoring as automatic, what is meant is that the individual analyte measurements that make up the monitoring protocol are made according to a schedule, typically under the direction of an automatic activation means, as described in greater detail infra. The predetermined scheduling modes can provide exact points in time at which measurements are to be made.

For predetermined "fixed interval" or periodic scheduling modes, a plurality of measurements are made during a given period of time when practicing the subject methods. While the number of measurements that are made in a given period of time necessarily varies at least in part with respect to the particular time period, the time interval or duration between measurements is the same. For example, where the period of time for collecting measurements is 8 hours, the number of measurements that are made is at least 4, usually at least 8 and more usually at least 16, where the number may be substantially higher, e.g., 24, 36, 48, or higher, depending on the desired frequency of analyte concentration measurement for the 8 hour period. Therefore, in a given period of time, individual analyte concentration measurements may be made every 5 minutes, every ten minutes, every 0.5 hours, every hour, every 2 hours, every 4 hours, etc. For example, if measurements are to be made every ten minutes during an 8 hour time period, the predetermined schedule employed in the subject method would provide for measurements to be taken at t=10 minutes, t=20 minutes, t=30 minutes, t=40 minutes, t=50 minutes and t=60 minutes, etc., as measured from t=0, representing the start of testing. The particular periodicity of analyte concentration measurements that are made during a given time period when practicing the subject methods is not critical, so long as at least two measurements are made during the time period such that the analyte concentration is monitored, and not just measured once.

For predetermined "fixed time" scheduling modes, a plurality of measurements are also made during a given period of time when practicing the subject methods. However, the interval at which the measurements are conducted are not fixed but are pre-selected for certain times of the day or night, such as 8 am, 9 am, 10:30 am and 11 am. This predetermined schedule can be programmed into the activation means by either the patient or the healthcare provider.

In other scheduling modes, the activation by which the measurement means is initiated can be based on data previously obtained within a certain period. This type of scheduling mode may be adaptive or predictive. In an adaptive mode, measurements are activated based on data received or collected in the recent past, such as within the last 0.5 to 12 hours, for example. In a predictive mode, measurements are activated based on data received or collected over a greater period of time such as within the last day or two. Such types of scheduling modes may be adjunct to a predetermined scheduling mode wherein the adaptive or predictive mode is activated based on previous measurement criteria which may be out of a certain specified range, e.g., one that indicates a rise or fall in the analyte concentration. For example, with diabetic patients, an adaptive mode may be activated where several of the more recent analyte measurements indicate that the change in glucose concentration level is too rapid. With such patients, a predictive mode may be activated if previous measurements indicate a swing in glucose levels during, for example, the early morning hours over the last few days. The new scheduling patterns invoked by the adaptive or predictive modes may themselves be predetermined with either fixed, partially fixed or unfixed measurement intervals. For example, in the case of the diabetic who has recently experienced a sharp rise or fall in his glucose concentration level which has triggered an adaptive measurement scheduling mode, a 5 minute-interval measurement schedule may be invoked to closely monitor the glucose level if the situation warrants additional measures, e.g., an immediate intake of glucose. In the situation where changes in glucose levels generally occur during a certain time of day and, thus, activate a predictive scheduling mode, measurements may then be scheduled at 0.5 hour-intervals during the hours from 5 am to 9 am, for example, and then revert to a more typical measurement schedule during the rest of the day.

The present invention also provides for the optional feature of scheduling "on-demand" in which the patient or healthcare provider manually overrides the current scheduling mode and immediately activates the measurement means. For example, a diabetic patient may desire to know his or her current glucose level before and/or after eating a food having high sugar content. Upon an office visit by a patient, a physician may want to know the patient's current glucose level.

Another feature of the subject methods is that each analyte concentration measurement made during a given monitoring protocol is made with a substantially painless single use analyte concentration measurement means. By "single-use" is meant that the analyte concentration means is one that is used only once, and then not used again for analyte concentration measurement. As such, the analyte concentration measurement means employed in the subject invention are distinguished from the measurement means found in conventional implantable sensors in that the conventional implantable sensors are not single-use, i.e., they are used a plurality of times. The analyte concentration measurement means employed in the subject methods are preferably ones that are precalibrated, i.e., do not need to be adjusted prior to taking the anlayte measurement. By substantially painless it is meant that the analyte concentration means of the subject invention causes the host to experience little or no pain at any time during its use, e.g., during activation or measurement, such as insertion, sampling and withdrawal, while awake and during sleep.

As indicated above, the analyte concentration is monitored in the subject methods in a host or portion thereof Typically the analyte concentration is measured in a portion of a host, e.g., a biological fluid from a host. Biological fluids of interest include blood and fractions thereof, e.g., serum, plasma, etc., interstitial fluidand the like. In certain embodiments, the concentration of the analyte is measured in host biological fluid, where the observed measurement is then used to derive the concentration of the analyte in another portion of the host. For example, in certain embodiments the analyte concentration is measured in host interstitial fluid, where the measured value is then used to derive the value of the analyte in the host blood.

Because a feature of the subject methods is the use of substantially painless single use analyte concentration measurement devices, the biological fluid that is measured in many embodiments is interstitial fluid. Typically, the interstitial fluid (ISF) is obtained from skin, where the ISF may be obtained from any convenient portion(s) of the skin, e.g., the epidermal layer, dermal layer, subdermal layer, etc.

A variety of ISF analyte measurement means, i.e., measurement means for measuring an analyte in ISF fluid, have been developed and disclosed in the prior art, where these measurement means may be readily adapted for use in the present invention. These measurement means vary greatly in terms of configuration, nature of analyte detection and measurement, e.g., optical based, electrochemical etc., and the like. Representative measurement means of interest include, but are not limited to, those means disclosed in U.S. Pat. Nos. 5,746,217; 6,083,196; 5,591,139; 6,091,975 and the like, the disclosures of which are herein incorporated by reference.

In many embodiments, the measurement means will include a microneedle or analogous structure that is capable of being inserted into the skin in a substantially painless manner to sample ISF and measure the concentration of analyte in the resultant sampled/accessed ISF. Such microneedle measurement means are disclosed in the patents listed above and incorporated herein by reference. The measurement means may be designed to measure the analyte concentration in situ or ex vivo. As such, the measurement means may measure the concentration of the analyte without withdrawing the sample from the body, or may withdraw the sample from the body and then measure the analyte concentration in the withdrawn sample.

A variety of different analytes may be monitored using the subject methods, but the subject invention is particularly useful where the analyte of interest is glucose, because of the consequences of hypo- and hyperglycemia, if undetected over long periods.

In practicing the subject methods of monitoring analyte concentration in a host or portion thereof, two or more analyte concentration measurements are made during a given time period using separate or previously unused single use substantially painless analyte concentration measurement means, as described above, for each distinct or disparate measurement. The resultant measurements are then employed as a set as desired, depending on the particular application in which the subject monitoring step is being used, where representative applications are described in greater detail infra. The set of measured analyte concentrations may be used in raw form, or processed as desired, e.g., fit to a curve, etc., depending on the particular application in which the monitoring finds use. In this way, the analyte concentration is monitored in a host, or portion thereof, eg., interstitial fluid.

Devices and Systems

Also provided are devices and systems for use in practicing the subject methods, as described above. The devices and systems of the subject invention include at least a first and second single use substantially painless analyte measurement means, as described above. As indicated above, the analyte measurements means of the subject devices may vary, depending on the particular region or portion of the host, the nature of the sample, the nature of the analyte, etc., where the measurement means may employ optical measurement, electrochemical measurement, or other specific measurement means. In many embodiments, the measurement means of the subject devices are ISF analyte concentration measurement means, as reviewed above.

While the device and systems of the subject invention include at least a first and second analyte measurement means, they typically include more than two measurement means, where the number of measurement means may be 4, 8, 16, 24 or higher, depending on the particular nature of the device.

In certain embodiments, the measurement means may be present on a cartridge or analogous means that can be separated or removed from the remainder of the device, such that when all of the measurement means of a given cartridge are employed, the cartridge may be removed and replaced with another cartridge, such that the whole device need not be discarded. In yet other embodiments, the measurement means may be integral and non-removable from the remainder of the device, such that when the last of the measurement means is employed, the device is discarded. Because of the lower cost and efficiency of resource use provided by the cartridge embodiments of the device, embodiments that include a removable cartridge that provides for the measurement means are preferred in many embodiments.

In addition to the measurement means, the subject devices and systems also include a measurement activation means. The measurement activation means is a means capable of activating each of the measurement means of the device according to a predetermined or pre-set schedule. Typically, the activation means is made up of suitable hardware and software components, e.g., a microprocessor under the control of a suitable algorithm, that provide for selective activation of each of the measurement means according to the desired predetermined schedule. In other words, the various components that make up the activation means are capable of activating each of the measurement means according to the measurement scheduling mode that controls the activation means. Typically, the activation means includes an algorithm that provides the instructions to the hardware component of the activation means for activating each of the measurement means according to the selected scheduling mode. The particular nature of the activation means is not critical to the device, so long as it is capable of providing for activation of the measurement means according to the desired predetermined schedule. The activation means may be readily generated from currently known and available components without undue experimentation on the part of one ordinarily skilled in the art.

The activation means that is present in the device may be a "learning" activation means, in that it may be able to automatically modify a predetermined activation schedule according to which it activates the individual measurement means, where the modification of the schedule is based on previous analyte concentration measurements and trends thereof, e.g., patterns of analyte concentration observed by the activation means. For example, where the analyte is glucose and initial measurements made according to the predetermined schedule indicate a rapid decrease in glucose concentration that warrant an increase in the measurement frequency, the activation means may be programmed to recognize such a pattern and change or adapt the activation frequency accordingly.

In addition to the activation means that automatically activate each individual measurement means of the device, the device may also include a means for manually activating a measurement means on command. For example, the device may include a button, lever or analogous means that can be manipulated at will to provide for an instant measurement of analyte concentration "on-demand".

The device may also include a processing means for collecting the raw analyte concentration measurement data from the measurement means and processing it as needed/desired into a final desired format. As such, the processing means may include date processing algorithms that convert the data into a desired format, e.g., into linear functions, etc., that correlate the data to analyte concentration of another portion of the host, e.g., that convert ISF concentration into the blood concentration; and the like.

In addition, the devices may have a readout means that displays the monitored analyte concentration. Any convenient readout or display means may be employed, including an LCD, etc, where the display means may display the data in any convenient format, e.g., numerically, graphically, etc.

The device and systems may take a variety of different configurations. In certain embodiments, the devices are single, integral devices, in which the measurement means, processing means, display means etc. are all present on the same structure. In yet other embodiments, one or more of the components may be separate from the other components. For example, the measurement means may be separated from the display means, where telemetric communication or analysis data transmission means, e.g., radio frequency or RF means, are employed to provide for data communication between the two or more disparate components of the device.

One representative device embodiment is a "watch" embodiment, in which the device is configured to be worn around a limbic portion, e.g., a wrist, in a manner analogous to a watch. In this embodiment, all of the components of the device may be present in one integral unit, where the unit is maintained in contact with the skin of the host via an adjustable strap or other retention means. Where the device is to contact a portion of the host that is not readily viewable, e.g., a portion of the waist or other portion that is typically covered by clothes or otherwise not readily viewable, the two component device may be employed, where the measurement means, e.g., sample pads and sensors, are one component of the device and the display or readout means is present on the other component of the device. The two disparate components communicate with each other a data communication means, where the data communication means is typically a wireless data communication means, e.g., RF telemetric means.

Utility

The subject methods, devices and systems find use in a variety of different applications in which monitoring the concentration of an analyte in a body sample over a given period of time is desired. As such, the subject methods may be employed to: (a) continuously or periodically monitor an analyte whose concentration is associated with a disease condition, e.g., hypo-or hyperglycemia in blood sugar disorders such as diabetes; (b) continuously or periodically monitor an analyte whose concentration is associated with a non-disease physiological condition of interest, e.g., alcohol intoxication, illegal drug use; (c) continuously or periodically monitor the concentration of a therapeutic agent in drug therapy applications; etc.

Where the analyte is glucose, the subject methods find use in a variety of different applications relating to the treatment and management of glucose-associated disease conditions, e.g., diabetes and related conditions. In these embodiments, the subject methods and devices find use in providing for "continual" glucose monitoring, by which is meant that glucose levels in a patient are measured intermittently and automatically according to a predetermined schedule. The subject methods therefore find use in the management of glucose blood levels in glucose metabolism associated disease conditions, by providing for a means to continually monitor the concentration of blood glucose and intervene in an appropriate manner where necessary, e.g., by administration of insulin, by ingestion of sugar, and the like. The subject methods can also be employed to detect and predict the occurrence of hypo- and hyperglycemic conditions. In such applications, the pattern of continually monitored analyte concentration measurements can be employed to determine whether a patient is experiencing hyper or hypo glycemia by comparing the pattern to a control or reference pattern. In addition, one can look at a pattern of measurements and compare it to an appropriate control or reference pattern to predict the occurrence of a hypo or hyperglycemic condition. The subject methods can be part of a more comprehensive therapy protocol designed to prevent the occurrence of hypo and hyperglycemic events, e.g., by predicting the occurrence of such events with the subject methods and device and intervening in blood sugar metabolism in a manner that prevents the occurrence of the predicted event, e.g., via insulin injection or glucose ingestion.

The subject methods and devices find use with a variety of different types of hosts where analyte monitoring is desired. Hosts of interest include, but are not limited to mammals. Mammals of interest include valuable livestock, e.g., horses, cows, sheeps, etc., pets, e.g., dogs, cats etc., and humans. In most embodiments, the mammals on which the subject methods are practiced are humans.

Kits

Also provided are kits for practicing the subject methods. In one embodiment, the kits include a device for practicing the subject invention. The device may be a single integral device or made up of two or more disparate components, e.g., a display component and a measurement component. In certain embodiments, the device may be a device in which the measurement means are present on a removable cartridge. in such embodiments, the kits may include a single cartridge, or two or more cartridges. In yet other embodiments, the subject kits may include one or more cartridges for use in a disparate device not included in the kit. Finally, the kits typically include instructions for using the subject reagent test strips in the determination of an analyte concentration in a physiological sample. These instructions may be present on one or more of the packaging, a label insert, containers present in the kits, and the like.

The subject methods and devices provide continual measurement of an analyte of interest without the problems experienced with implantable analyte sensors. For example, because single-use substantially painless analyte measurement means are employed, user irritation and pain are avoided. Furthermore, the individual measurement means employed need not be calibrated prior to use. In addition, with respect to the glucose the subject devices and methods can not only be employed to rapidly and accurately detect the occurrence of a hypo or hyperglycemic event with out host participation, but they can also be employed to readily predict the occurrence of hypo and hyperglycemic conditions, and therefore provide for improved management of blood glucose metabolism associated disease conditions. As such, the subject invention represents a significant contribution to the art.

All publications and patents cited in this specification are herein incorporated by reference as if each individual publication or patent were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of monitoring the concentration of analyte in a host over a given time period, said method comprising:
   (a) making a first analyte concentration measurement in said host at a first point in said time period using a first single use analyte concentration measurement means;
   (b) making a second analyte concentration measurement in said host at a second point in said time period using a second single use analyte concentration measurement means,
      wherein said analyte concentration measurements are made according to a selected scheduling mode to monitor the concentration of said analyte in said host over said given time period; and
   (c) making one or more additional analyte concentration measurements during said time period using one or more additional single use analyte concentration measurement means;
      wherein said time period of said additional measurements is based on results of said first and second measurements.

2. The method according to claim 1, wherein said host is interstitial fluid.

3. The method according to claim 2, wherein said single use analyte concentration measurement means is an interstitial fluid analyte measurement means.

4. The method according to claim 3, wherein said interstitial fluid analyte measurement means makes an in situ analyte concentration measurement.

5. The method according to claim 3, wherein said interstitial fluid analyte concentration measurement means removes interstitial fluid from said host and analyzes said fluid outside of said host.

6. The method according to claim 3, wherein said interstitial fluid analyte concentration measurement means comprises a microneedle.

7. The method according to claim 1, wherein said analyte is glucose.

8. The method according to claim 1, wherein the selected scheduling mode comprises a predetermined schedule.

9. The method according to claim 8, wherein the predetermined schedule comprises measurements taken at fixed time intervals.

10. The method according to claim 8, wherein the predetermined schedule comprises measurements taken at fixed times.

11. The method according to claim 1, wherein the selected scheduling mode comprises a scheduling mode responsive to previously collected analyte concentration measurements.

12. The method according to claim 11, wherein the previously collected analyte concentration measurements were taken over the previous 48 hours.

13. The method according to claim 11, wherein the previously collected analyte concentration measurements were taken over the previous two hours or less.

14. A method of monitoring the concentration of glucose in interstitial fluid of a host over a given period of time, said method comprising:
(a) making a first interstitial fluid glucose concentration measurement at a first point in said time period using a first single use fluid glucose concentration measurement means;
(b) making a second interstitial fluid glucose concentration measurement at a second point in said time period using a second single use fluid glucose concentration measurement means;
wherein said analyte concentration measurements are made according to a selected scheduling mode to monitor the concentration of said analyte in said host over said given time period; and
(c) making one or more additional analyte concentration measurements during said time period using one or more additional single use interstitial fluid glucose concentration measurement means;
wherein said time period of said additional measurements is based on results of said first and second measurements.

15. The method according to claim 14, wherein said interstitial fluid glucose measurement means makes an in situ measurement.

16. The method according to claim 15, wherein said interstitial fluid analyte concentration measurement means removes interstitial fluid from said host and analyzes said fluid outside of said host.

17. The method according to claim 14, wherein said interstitial fluid glucose concentration measurement means comprises a microneedle.

18. The method according to claim 14, wherein said method employs a device that comprises:
(a) at least said first and second interstitial fluid glucose measurement means; and
(b) an activation means that activates said first and second measurement means according to a predetermined schedule.

19. The method according to claim 18, wherein said activation means comprises hardware and software components that activate said first and second measurement means according to said predetermined schedule.

* * * * *